[11] Patent Number: 4,569,790
Koths et al.
[45] Date of Patent: Feb. 11, 1986

[54] PROCESS FOR RECOVERING MICROBIALLY PRODUCED INTERLEUKIN-2 AND PURIFIED RECOMBINANT INTERLEUKIN-2 COMPOSITIONS

[75] Inventors: Kirston Koths, Berkeley; James Thomson, Albany; Michael Kunitani, Oakland; Kenneth Wilson, Walnut Creek; Wolf Hanisch, Oakland, all of Calif.

[73] Assignee: Cetus Corporation, Emeryville, Calif.

[21] Appl. No.: 594,223

[22] Filed: Mar. 28, 1984

[51] Int. Cl.[4] .......................... C07K 3/12; C12D 21/02
[52] U.S. Cl. .......................... 260/112 R; 260/112.5 R; 435/68; 435/172.3
[58] Field of Search .................... 260/112 R, 112.5 R; 435/170, 172, 849, 68

[56] References Cited

U.S. PATENT DOCUMENTS

| | | | |
|---|---|---|---|
| 4,315,852 | 2/1982 | Leibowitz et al. | 435/811 |
| 4,450,103 | 5/1984 | Konrad et al. | 260/112 R |
| 4,462,940 | 7/1984 | Hanisch et al. | 435/68 |
| 4,464,295 | 8/1984 | Laduri et al. | 260/112 R |
| 4,464,355 | 8/1984 | Fabricius et al. | 424/101 |
| 4,476,049 | 10/1984 | Kung | 260/112 R |
| 4,490,289 | 12/1984 | Stern et al. | 260/112 |
| 4,511,502 | 4/1985 | Builder et al. | 260/112 R |
| 4,511,503 | 4/1985 | Olson et al. | 260/112 R |
| 4,512,922 | 4/1985 | Jones et al. | 260/112 R |

FOREIGN PATENT DOCUMENTS

| | | | |
|---|---|---|---|
| 83103582.9 | 10/1983 | European Pat. Off. | |
| 92163 | 10/1983 | European Pat. Off. | |
| 83400938.3 | 11/1983 | European Pat. Off. | |
| 94317 | 11/1983 | European Pat. Off. | |
| 118977 | 9/1984 | European Pat. Off. | |
| 119621 | 9/1984 | European Pat. Off. | |
| 0121352 | 10/1984 | European Pat. Off. | 435/68 |
| 0128467 | 12/1984 | European Pat. Off. | 435/68 |
| 147819 | 7/1985 | European Pat. Off. | |
| 0148098 | 11/1980 | Japan | 435/68 |

OTHER PUBLICATIONS

Watson et al., *J. Exp. Med.*, (1979), 150:849–861.
Gillis et al., "*J. Immunol.*, (1980), 124:1954–1962.
Mochizuki et al., *J. Immuno. Meth.*, (1980), 39:185–201.
Welte K. et al., *J. Exp. Med.*, (1982), 156:454–464.
Derynel R. et al., *Nature*, (1980), 287, 193–197.
Zaniguchi et al., *Nature*, (1983), 302, p. 305, Structure and Expression of a Cloned . . . IL-2.
*Lymphotine Res.* 1(2) 1982, FASEB 1982 Editorial.
*J. Immunol.* 129(6), 1982, Ihle et al., p. 2431, Procedures for the Purification of IL–3 to Homogeniety.
Milestone et al., Purification of T-Cell Growth Factor to Homogeneity by RP-HPLC, *Biochem. Biophy. Res. Comm.* 115(3) 1983, pp. 762–768 (1983).
Henriksen et al., Control of the Expression of IL-2 Activity, *Cell. Immunol.* 73 (1982), pp. 106–114.
Henderson et al., A Rapid, Large Scale Purification Procedure for Gibbon IL-2, *J. Immunol.* 131(2) (1983), pp. 810–815.

(List continued on next page.)

*Primary Examiner*—John Kight
*Assistant Examiner*—Garnette D. Draper
*Attorney, Agent, or Firm*—Albert P. Halluin; Thomas Ciotti

[57] ABSTRACT

A process for recovering microbially produced IL-2 in a highly pure form from the cellular material of the microorganisms that produced it comprising: disrupting the cell membranes of the microorganisms; extracting the disruptate with a chaotropic agent, such as urea, that selectively extracts microbial proteins from the cellular material; solubilizing the IL-2 in the solid phase of the extraction mixture with an aqueous solution of a solubilizing agent, such as SDS, containing a reducing agent; and separating the IL-2 from the resulting solution by an optional extraction with 2-butanol or 2-methyl-2-butanol followed by gel filtration chromatography, oxidizing the IL-2 and purifying the oxidized IL-2 by RP-HPLC.

21 Claims, 4 Drawing Figures

DENSITOMETRY SCANS OF 15% SDS PAGE

1

PROCESS FOR RECOVERING MICROBIALLY PRODUCED INTERLEUKIN-2 AND PURIFIED RECOMBINANT INTERLEUKIN-2 COMPOSITIONS

TECHNICAL FIELD

This invention is in the field of biochemical engineering. More particularly, the invention concerns a biochemical separation or recovery process in which interleukin-2 (IL-2) is separated or recovered from microorganisms that have been transformed to produce IL-2.

BACKGROUND ART

Native human IL-2 is an antigen-nonspecific, genetically unrestricted soluble factor produced by erythrocyte rosette positive T cells stimulated with antigens, mitogens and alloantigens. It is a protein with a reported molecular weight in the approximate range of 13,000 to 17,000 daltons (S. Gillis and J. Watson, *J Exp Med* (1980) 159:1709) and an isoelectric point in the approximate range of pH 6-8.5. Human IL-2 has a number of in vitro and in vivo effects including enhancing the proliferative responses of human peripheral blood mononuclear cells or murine thymocytes, enhancing the immune response in humans and in animals against bacterial, parasitic, fungal, protozoan and viral infections, and supporting the growth of continuous T cell lines.

IL-2 and IL-2 muteins in which the cysteine residue at amino acid 125 has been replaced with serine and/or the initial alanine has been eliminated have been produced microbially through genetic engineering techniques. Microbially produced IL-2 is not glycosylated and is produced in a reduced-state by the microorganisms. When purified and oxidized, these microbially produced IL-2s exhibit activity comparable to native human IL-2.

Procedures for purifying native IL-2 from T cells are described by Watson, J., et al, *J Exp Med* (1979) 150;849-861; Gillis, S., et al, *J Immunology* (1980) 124:1954-1962; Mochizuki, D. Y., et al, *J Immun Meth* (1980) 39:185-201; Welte, K., et al, *J Exp Med* (1982) 156:454-464; and European patent applications No. 83103582.9 (published 26 Oct. 1983 under No. 92163) and No. 83400938.3 (published 16 Nov. 1983 under No. 94317). In general these procedures involve precipitating proteins from culture supernatants with ammonium sulfate followed by a chromatographic fractionation.

Commonly owned copending U.S. patent application Ser. No. 353,360, filed 1 Mar. 1982 and Derynck, R., et al, *Nature* (1980) 287:193-197 describe procedures for recovering IFN-β from IFN-β-producing *E. coli.* The patent application describes a procedure in which IFN-β is extracted from cellular material with 2-butanol or 2-methyl-2-butanol.

DISCLOSURE OF THE INVENTION

The invention is a process for recovering IL-2 from an IL-2-producing microorganism comprising:

(a) disrupting the cell membrane of the microorganism;

(b) extracting the disruptate with an aqueous solution of a chaotropic agent;

(c) solubilizing the IL-2 in the solid phase of the extraction mixture with an aqueous solution of a solubilizing agent that forms a water soluble complex with the IL-2, said solution containing a reducing agent; and (d) separating the IL-2 from the resulting solution in the presence of a reducing agent.

In preferred embodiments of this process the chaotropic agent is urea at a concentration of about 3.5 M to about 4.5 M in the extraction mixture, the solubilizing agent is sodium dodecyl sulfate (SDS) or sodium lauryl sarcosine (sarcosyl), the solubilized IL-2 is further extracted with 2-butanol or 2-methyl-2-butanol and the final separation is carried out by gel filtration, the resulting sized product is oxidized and the oxidized product is purified by reverse-phase high performance liquid chromatography (RP-HPLC).

MODES FOR CARRYING OUT THE INVENTION

Figure 1:
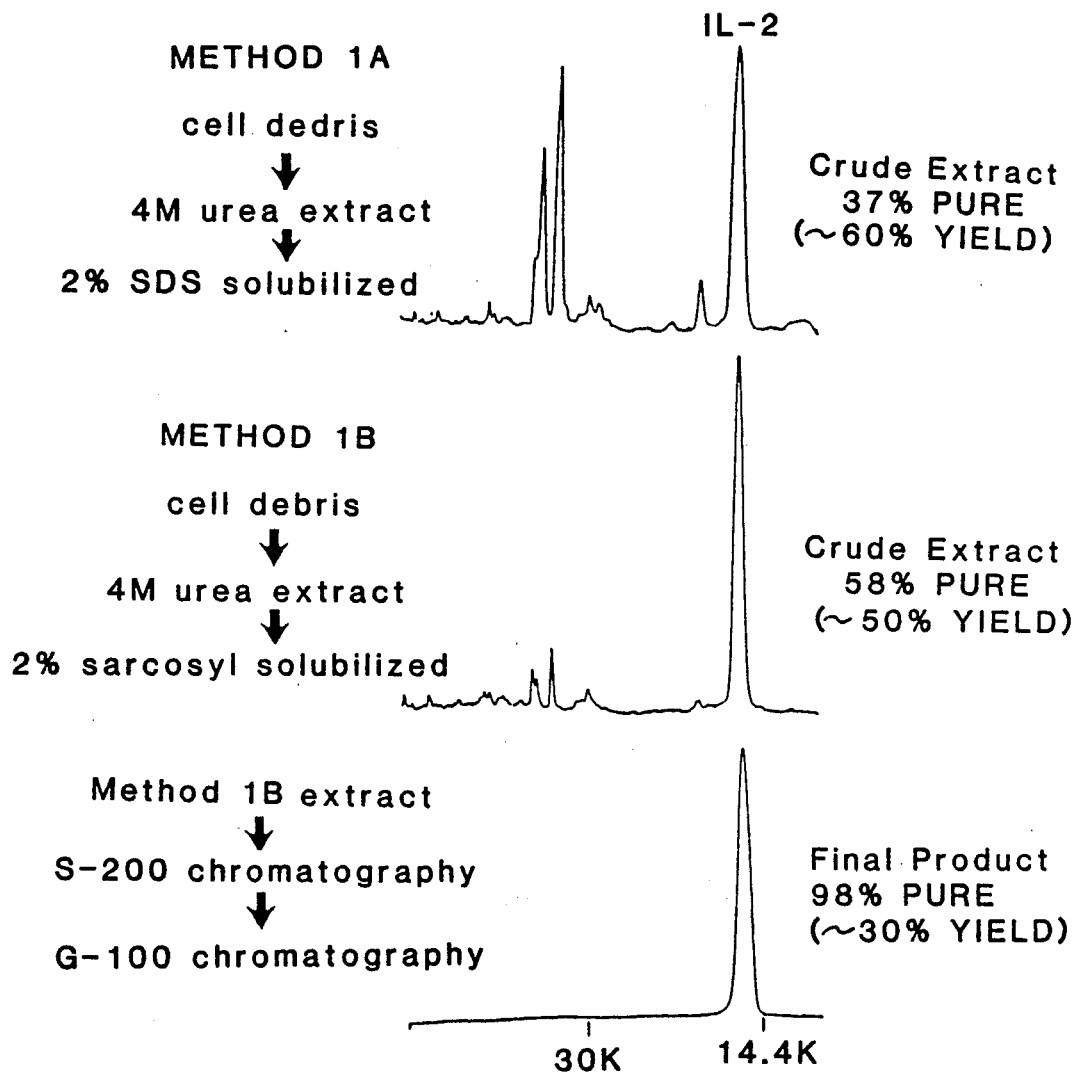
FIG. 1 shows a flow diagram of two alternative embodiments of the invention process in which gel filtration chromatography is used as a final purification step. The embodiment designated Method 1A uses SDS as a solubilizing agent; the embodiment designated Method 1B uses sarcosyl as a solubilizing agent. The figure includes densitometer scans of SDS-polyacrylamide gel electrophoresis (SDS-PAGE) analyses of the product at various steps in the process.

As used herein the term "IL-2" denotes an unglycosylated protein that is (a) produced by a microorganism that has been transformed with a human interleukin-2 gene or a modification of the human interleukin-2 gene that encodes a protein having: (a) an amino acid sequence that is at least substantially identical to the amino acid sequence of native human interleukin-2 and (b) has biological activity that is common to native human interleukin-2. Substantial identity of amino acid sequences means the sequences are identical or differ by one or more amino acid alterations (deletions, additions, substitutions) that do not cause an adverse functional dissimilarity between the synthetic protein and native human interleukin-2. Examples of such proteins are the IL-2s described in European patent application No. 83101035.0 filed 3 Feb. 1983 (published 19 Oct. 1983 under publication No. 91539) and European patent application No. 82307036.2 filed 22 Dec. 1982 (published 14 Sept. 1983 under No. 88195), the IL-2s described in commonly owned U.S. Ser. No. 564,224, filed 20 Dec. 1983, now U.S. Pat. No. 4,518,584, issued May 21, 1985, which description is incorporated herein by reference, and the IL-2s described in the examples of this application.

As used herein the term "transformed microorganism" denotes a microorganism that has been genetically engineered to produce a protein that possesses native human interleukin-2 activity. Examples of transformed microorganisms are described in said European patent publications Nos. 88195 and 91539, said U.S. Pat. No. 4,518,584 and the examples of this application. Bacteria are preferred microorganisms for producing IL-2. Synthetic IL-2 may also be made by suitably transformed yeast and mammalian cells. *E. coli* is particularly preferred.

The transformed microorganisms are grown in a suitable growth medium, typically to an optical density (OD) of at least about 30 at 680 nm, and preferably between about 20 and 40 at 680 nm. The composition of the growth medium will depend upon the particular microorganism involved. The medium is an aqueous medium containing compounds that fulfill the nutritional requirements of the microorganism. Growth media will typically contain assimilable sources of carbon and nitrogen, energy sources, magnesium, potassium and sodium ions, and optionally amino acids and purine and pyrimidine bases. (See *Review of Medical Biology*. Lange Medical Publications, 14th Ed pp 80–85 (1980).) In expression vectors involving the trp promoter, the tryptophane concentration in the medium is carefully controlled to become limiting at the time IL-2 expression is desired. Growth media for *E. coli* are well known in the art.

After the cells are harvested from the culture, they may be concentrated, if necessary, to about 20 to 150 mg/ml, preferably 80 to 100 mg/ml (OD 40 to 300, preferably 160 to 200 at 680 nm) by filtration, centrifugation, or other conventional methods.

Following concentration the cell membranes of the microorganisms are disrupted. The main purpose of disruption is to facilitate the following extraction and solubilization steps. Conventional cell disruption techniques such as homogenization, sonication, or pressure cycling may be used in this step of the process. Preferred methods are sonication or homogenization with a Manton-Gaulin homogenizer. The end point of the disruption step may be monitored by optical density, with the optical density of the suspension typically decreasing about 65% to 85%. In any event, the disruption should break substantially all of the cells so that substantially no intact cells are carried through to the solubilization step. Before the disruption, the pH of the liquid phase of the concentrate is adjusted, if necessary, to a level that facilitates removal of *E. coli* proteins in subsequent steps, while retaining IL-2 protein as an insoluble complex in the celluar debris. The pH may be so adjusted by adding suitable buffers. In most instances pHs in the range of about 8 to about 8.5 will be used.

The steps in the recovery process subsequent to the disruption step are primarily designed to separate the IL-2 from *E. coli* proteins to a high level of purity (preferably at least about 95% and more preferably at least about 98%) in good yields while maintaining the IL-2 in a reduced state. Simultaneously, these purification processes, in combination, also reduce pyrogenic substances in the final product to a level believed to be acceptable for patenteral administration to patients.

After the cells have been disrupted the particulate matter may be separated from the liquid phase of the disruptate and resuspended in an aqueous medium buffered to the optimal pH for the extraction. The particulate matter may optionally be washed with buffer at this stage to remove any water soluble *E. coli* proteins therein. In any event, the protein concentration of the cell suspension subjected to the extraction will usually be in the range of about 5 to about 60 mg/ml, preferably 20 to 40 mg/ml.

The extraction of *E. coli* proteins from the particulate cellular material may be carried out concurrently with the disruption or sequentially following the disruption. It is preferably carried out as a separate step following the disruption. The extractant is an aqueous solution of a chaotropic agent (i.e., a mild protein denaturant that dissociates hydrogen bonds and affects the tertiary structure of proteins). The extractant selectively removes the bulk of the *E. coli* proteins from the cellular debris leaving at least a substantial portion of the IL-2 associated (contained in or bound to) with the cellular debris. The selectivity is facilitated by the hydrophobicity of the IL-2 and the fact that it is in a reduced, insoluble state at a pH near the isoelectric point of the protein. In addition, a substantial portion of the IL-2 may be present in vivo as inclusion bodies of significant mass, as has been the case with other cloned proteins expressed at high levels in *E. coli*. Examples of extractants are urea and guanidinium hydrochloride (guanidinium hydrochloride should not be used when SDS is used as a solubilizing agent). Urea is preferred. The concentration of the chaotropic agent in the extraction mixture will depend upon the particular agent that is used and the amount of cellular material in the extraction mixture. In the case of urea, concentrations (final) between about 3.5 M and 4.5 M, preferably about 4 M, will be used in batch processes at 25° C. If the extraction is run on a continuous basis over longer time periods it may be desirable to use lower concentrations. Temperatures in the range of 20° C. to 25° C. will normally be used in extraction, with room temperature being used for convenience. Mixing will typically be used to enhance contact between the solution and particulate matter and thus decrease the time required to extract non-IL-2 proteins from the cellular debris. Kinetic analysis of the extraction process was performed on the supernatants using SDS-PAGE, and the extraction was found to be essentially complete by 15–30 min.

Following the extraction, the mixture is separated into solid and liquid phases. The IL-2 in the solid phase is then selectively solubilized by contacting the solid phase with a neutral, aqueous buffer containing a reducing agent and a solubilizing agent. Surface active agents (detergents) that have a suitable hydrophobic-hydrophilic balance to solubilize the hydrophobic IL-2 may be used. Alkali metal sulfates containing 10 to 14 carbon atoms and alkali metal alkyl sarcosinates are preferred solubilizing agents, with SDS and sarcosyl being particularly preferred.

The amount of solubilizing agent used in the solubilization will depend upon the particular agent. When SDS or sarcosyl are used, the preferred ratio (w/w) of SDS/sarcosyl to solid phase protein is about 0.5:1 to 1.4:1. The solubilizing medium also contains a sufficient amount of reducing agent to prevent the solubilized IL-2 from undergoing oxidation to any significant degree. Protein reducing agents such as dithiothreitol (DTT) and 2-mercaptoethanol may be used. The concentration of reducing agent such as DTT in the medium will usually range between about 5 to 20 mM. The solubilization will typically be carried out at temperatures in the range of 20° C. to 25° C. with mixing to facilitate contact between the solid phase and the solubilizing medium. Higher temperatures may solubilize unwanted *E. coli* proteins. The solubilization is considered complete when the sample has sat 15 min or the solution turns translucent. Insoluble material is separated after completing the solubilization.

After the IL-2 is solubilized the IL-2 may optionally be extracted from the aqueous solution under reducing conditions with 2-butanol or 2-methyl-2-butanol to remove additional *E. coli* proteins, notably including certain contaminants that have molecular weights very close to the IL-2. Conditions (e.g., ionic strengths in the range of 0.05 and 0.15) at which the aqueous solution and butanol are substantially immiscible are used. In carrying out the organic extraction the protein concentration of the aqueous solution is preferably adjusted, if necessary, to less than about 6 mg/ml, preferably about 0.5 to 4 mg/ml. Reducing conditions are maintained by carrying out the extraction in the presence of a reducing agent (e.g., DTT). The butanol will normally be added to the aqueous solution of solubilized IL-2 in volume ratios in the range of about 1:1 to about 3:1 (extractant-:aqueous solution), preferably about 1:1. The extraction may be carried out in a batch or continuous operation. The temperature will normally be in the range of 20° C. to 100° C. and the pH will normally be about 4 to 9, preferably about 5 to 6. The time of contact between the solution and the butanol is not critical and relatively short times on the order of a few minutes may be used. After the extraction is complete, the aqueous phase and butanol phase are separated and the IL-2 is separated from the butanol phase. A preferred procedure for separating the IL-2 from the butanol phase is acid precipitation. This is done by adding the butanol phase to aqueous buffer, pH 7.5 until the organic phase is dissolved (approx. 2–3 vol buffer per vol of organic), and then lowering the pH to about 5.5 to 7.0, preferably 6.0 to 6.2, to cause the IL-2 to precipitate.

The next step in the process is to separate the IL-2 and any *E. coli* contaminants remaining after the extraction(s) and optimally from the solubilizing agent. Gel filtration chromatography, RP-HPLC, or a combination of gel filtration chromatography and RP-HPLC are used. The gel filtration chromatography is preferably carried out in two stages that remove both pyrogenic components and protein contaminants having molecular weights higher or lower than IL-2. (IL-2 has a molecular weight of about 15.5K daltons.) Gels that are capable of fractionating the solution to permit separation of the IL-2 from these contaminants are commercially available. Sephacryl S-200 is a preferred gel for removing the higher molecular weight components and Sephadex G-25, G-75 or G-100 gels are preferred for removing the low molecular weight contaminants. The gel filtrations will typically be run in buffered solutions (pH 5.5 to 7.0) containing about 0.1% to 1.0% solubilizing agent and about 1 to 10 mM reducing agent. The column will be sized to permit suitable resolution of the desired components.

RP-HPLC is an alternative to gel filtration. Also, RP-HPLC is capable of removing molecules from the solution that have molecular weights close to IL-2 and cannot, therefore, be removed completely by gel filtration. In addition, contaminants such as bacterial endotoxin are also removed effectively by RP-HPLC. Therefore, RP-HPLC may also be used as a final purification step after gel filtration. Supports (stationary phases) that provide good resolution of proteins may be used in the RP-HPLC. C-4, C-8, or C-18 on 300 angstrom pore-size supports are examples of preferred supports. The separation is carried out at an acidic pH of less than about 2.3, usually 2.1 to 2.3, in order to keep the IL-2 in solution. In this regard, the pH of the solution from the solubilization (gel filtration) will preferably be adjusted to this range. The solution is loaded into the RP-HPLC column and is adsorbed onto the stationary phase. A gradient solvent system comprising an organic acid such as acetic acid or trifluoroacetic acid and organic solvent such as propanol or acetonitrile is used to elute the IL-2 from the column. Acetic acid-propanol, trifluoroacetic acid-propanol, and trifluoroacetic acid-acetonitrile are preferred solvent systems. IL-2 elutes in the acetic acid-propanol system at about 40% propanol, in the trifluoroacetic acid-propanol system at about 50% propanol, and in the trifluoroacetic acid-acetonitrile system at about 62% acetonitrile. For convenience, the organic solvent content of the elutant will usually be increased rapidly to a level somewhat below the solvent concentration at which the IL-2 elutes followed by a slow gradient change in the range of about 0.1% to 1.0%/min.

As soon as the IL-2 is recovered from the chromatography step, it is lyophilized and resuspended in a neutral aqueous buffer containing the reducing agent (to keep the IL-2 in a reduced state) and the solubilizing agent (to keep it in solution). The IL-2 is stable in this form and may be stored for further treatment and formulation before being used.

An alternative and preferred procedure is to oxidize the IL-2 after it has been separated by gel filtration and purify the oxidized product by RP-HPLC or gel fitration followed by RP-HPLC. This results in efficient removal of contaminants surviving the gel filtration as well as unwanted oxidation products. A preferred oxidation procedure is described in a commonly owned U.S. patent application titled "Controlled Oxidation of Microbially Produced Cysteine-Containing Proteins", U.S. Ser. No. 594,351, filed Mar. 28, 1984, now abandoned in favor of U.S. Ser. No. 661,902, filed Oct. 17, 1984, U.S. Pat. No. 4,530,787. The relevant disclosure of that application is incorporated herein by reference. In said application Ser. No. 594,351 there is disclosed and claimed a preparative process for oxidizing fully reduced cysteine-containing microbially produced synthetic proteins, such as human IFN-$\beta$ or human IL-2, in a controlled manner so that the synthetic proteins have the same disulfide bridging as their native counterparts. The claimed process in said application includes oxidizing a fully reduced microbially produced synthetic protein having an amino acid sequence substantially identical to a useful protein which sequence includes cysteines which in the useful protein are linked intramolecularly to form a cystine in a controlled manner whereby said cysteines are oxidized selectively to form said cystine with minimal over-oxidation and formation of nonconforming cystine groups or oligomers comprising reacting the fully reduced microbially produced synthetic protein with o-iodosobenzoate in an aqueous medium at a pH at least about one-half pH unit below the pKa of said cysteines and wherein the concentration of synthetic protein in the reaction mixture is less than about 5 mg/ml and the mole ratio of o-iodosobenzoate to protein is at least stoichiometric, with the proviso that the o-iodosobenzoate is in excess in the terminal portion of the reaction. The process produces a novel cystine-containing protein, e.g., IL-2 preparation derived from synthetic microbially produced IL-2 having fully reduced cysteines comprising cystine-containing IL-2 which: (i) has the same disulfide bridging as native human IL-2; (ii) is substantially free of oligomers; and (iii) contains less than about 15% by weight of isomers, and preferably less than 1% by weight isomers, having disulfide bridging different from native human IL-2. RP-HPLC purification of the oxidized product may be carried out under the conditions described above in the absence of a reducing agent and presence of a detergent at a concentration equal to or less than those used in the above described gel filtration.

The purity of the IL-2 after the chromatography step(s) is at least about 95% and usually at least about 98%. This highly pure material contains less than about 5 ng endotoxin, usually less than about 0.01 ng endotoxin per 100,000 Units IL-2 activity.

The invention process is further described by the following examples. These examples are not intended to limit the invention in any manner.

EXAMPLE 1

IL-2 was recovered from *E. coli* K-12 strain MM294 that had been transformed with the plasmid pLW1 (deposited at the American Type Culture Collection on 4 Aug. 1983 under accession number 39,405) as follows.

The *E. coli* were grown in a fermenter using the following growth medium.

| | |
|---|---|
| $(NH_4)_2SO_4$ | 150 mM |
| $KH_2PO_4$ | 21.6 mM |
| $Na_3$ Citrate | 1.5 mM |
| $ZnSO_4.7H_2O$ | 30 mM |
| $MnSO_4.H_2O$ | 30 mM |
| $CuSO_4.5H_2O$ | 1 mM |
| pH adjusted to 6.50 with 2.5 N NaOH | |
| autoclaved | |
| Sterile Additions (post autoclave) | |
| $MgSO_4.7H_2O$ | 3 mM |
| $FeSO_4$ | 100 $\mu$M |
| L-tryptophan | 14 mg/l |
| Thiamine-HCl | 20 mg/l |
| Glucose | 5 g/l |
| Tetracycline | 5 mg/l |
| Ethanol (optional) | 2% |
| Casamino acids | 2% |

Dow Corning Antifoam B, 20% solution, glucose, 50% solution, and KOH, 5N, were added on demand.

The pH of the fermenter was maintained at 6.8 with 5N KOH. Residual glucose was maintained between 5–10 g/l, dissolved oxygen at 40%, and temperature at 37°±1° C. The casamino acids (20% stock solution) were added when the $OD_{680}$ was about 10. Harvest was made three hr after the $OD_{680}$ reached about 20.

The harvested material was concentrated by hollow fiber filtration and/or centrifugation. Twenty to forty g (wet weight) of the concentrate were resuspended in 200 ml of 50 mM Tris, 1 mM ethylenediaminetetraacetic acid (EDTA) (pH 8.1–8.5) (Tris/EDTA buffer). The suspension was centrifuged at 3,000–4,000×g for 10 min, the supernatant was removed, and the solids were resuspended in 200 ml Tris/EDTA buffer at 4° C. The suspension was loaded into a sonicator (Heat Systems, Model W-375) and sonicated at 4° C. for 45 min (end point=$OD_{680}$ reduction of about 85%) using large probe, pulsing with 50% duty on power setting "9". An alternative disruption technique is to pass the suspension three times through a Manton-Gaulin homogenizer on M-1 setting. Cellular debris was separated from the disruptate by centrifuging at 4,500×g for 10 min.

The cellular debris was resuspended in 60 ml Tris-/EDTA buffer at room temperature and an equal volume of 8 M urea (Schwarz/Mann ultrapure) in Tris-/EDTA buffer was added to the suspension over five min with rapid stirring (final urea concentration, 4 M). After continued slow stirring for 15–30 min, the suspension was centrifuged at 12,000×g for 15 min to recover extracted cellular debris. (If a solid phase does not form, the supernatant is withdrawn, an equal volume of Tris-/EDTA buffer is added and the mixture is recentrifuged.)

The extracted cellular debris is then resuspended in 9 ml of 50 mM sodium phosphate (pH 6.8), 1 mM EDTA, 10 mM DTT at 20° C. One ml of 20% SDS is added to the suspension, and the suspension is mixed vigorously for 5 min. The liquid phase is recovered from the suspension by centrifuging at 12,000×g for 10 min at room temperature. The liquid phase was then heated to 40° C. for 15 min to insure that the IL-2 in the solution is fully reduced. A sample of this crude extract was analyzed by 15% SDS-PAGE. FIG. 1 shows a densitometer scan of that analysis (product of Method 1A) indicating the extract contained about 37% IL-2.

IL-2 was separated from the solution by gel filtration chromatography as follows. The solution was loaded onto a 2.6 cm×100 cm S-200 column run in 50 mM sodium phosphate (pH 6.8), 1 mM EDTA, 1 mM DTT, 1% SDS. The column effluent was collected in 4 ml fractions with samples of the fractions analyzed in 15% SDS-PAGE minigels stained with Coomassie blue. The fractions containing the fewest contaminants (minimizing contaminants at about 35K daltons, 16–18K daltons, and 12K daltons) were pooled and concentrated to 5–10 ml by ultrafiltration (Amicon YM5 ultrafilter). The concentrate was loaded onto a 2.6 cm×100 cm G-100 column, run as above except that the SDS concentration was 0.1% rather than 1%. Fractions were analyzed by SDS-PAGE and the purest fractions were pooled. The drawing shows a densitometer scan of the chromatographed product. Analysis indicated the product was 98% pure and contained 0.5 ng endotoxin/100,000 units of IL-2 activity as measured by the limulus amebocyte lysate assay (Associates of Cape Cod, Inc., Woods Hole, MA). The N-terminal amino acid sequence of this IL-2 is the same as the native human molecule except that the initial N-terminal alanine is missing.

EXAMPLE 2

The procedure of Example 1 was repeated using 2% sarcosyl instead of 2% SDS as a solubilizing agent and using sarcosyl in place of SDS in the chromatography columns. FIG. 1 shows the densitometer scan for this crude extract using sarcosyl as a solubilizing agent (crude extract of Method 1B). As indicated, the use of sarcosyl in place of SDS gave improved purity (58% vs 37%) at similar IL-2 yield (50% vs 60%).

EXAMPLE 3

The procedure of Example 1 was repeated through the steps preceding urea extraction and was then solubilized and clarified as described.

Figure 2:
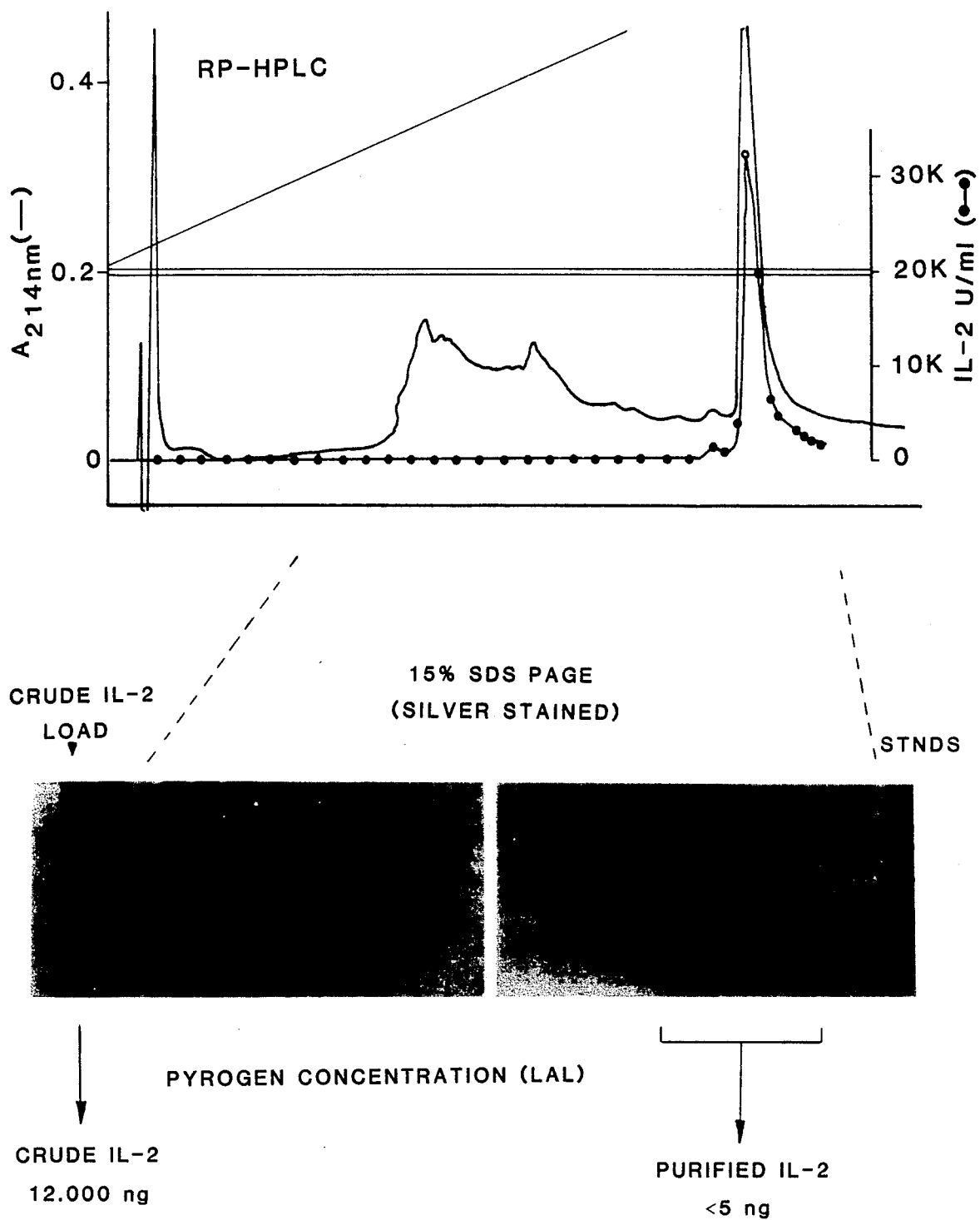
FIG. 2 is an HPLC chromatogram and SDS-PAGE analysis of the product of Example 3.

The IL-2 was separated from the solution by RP-HPLC as follows. The solution was diluted 10-fold in 0.1% trifluoroacetic acid (TFA) and was applied to a 4.6 mm I.D.×5 cm L. Brownlee Aquapore RP-300 column equilibrated in 0.1% TFA. The IL-2 was eluted with a gradient of 30%–60% acetonitrile containing 0.1% TFA over 45 min. The yield of IL-2 activity following HPLC was 80–100%. FIG. 2 shows a silver-stained SDS-PAGE analysis of this product.

EXAMPLE 4

The procedure of Example 1 was repeated through the steps preceding get filtration chromatography. The soluble, clarified, reduced material was subjected to G-100 chromatography in 0.1% SDS as described in Example 1. The pooled peak fractions of IL-2 were further purified by RP-HPLC as described in Example 3. The resulting purified, reduced IL-2 was oxidized and subjected to RP-HPLC as described in Example 3.

EXAMPLE 5

The procedure of Example 1 was repeated through the steps preceding the G-100 column. The procedure for Example 3 was repeated using a solvent system of propanol in 1 M acetic acid. The IL-2 was eluted with a gradient of 35%–60% propanol over 200 min. Column dimensions were either 10 mm ID×30 cm L or 48 mm ID×50 cm L, and the column was packed with a bonded phase wide-pore silica gel. The bonded phase wide-pore silica used was Vydac TP214. The purity and yield of product was comparable to that of Example 3.

EXAMPLE 6

The procedure of Example 3 was repeated using a solvent system of propanol in 0.1% TFA. The IL-2 was eluted with a gradient of 35%–60% propanol over 120 min. The column and support materials were the same as in Example 5. The purity and yield of product were comparable to that of Example 3.

EXAMPLE 7

The procedure of Example 1 was repeated except that the *E. coli*-produced IL-2 was one designated des-Ala Ser$_{125}$ IL-2. The amino acid sequence of this IL-2 is different from that of the native molecule in that the cysteine at position 125 has been changed to serine and the initial N-terminal alanine residue is missing. The *E. coli* that produce this IL-2 were made by the techniques described in said U.S. Ser. No. 4,518,584. Strains of des-Ala Ser$_{125}$ IL-2-producing *E. coli* were deposited in the American Type Culture Collection on Sept. 26, 1983 under accession number 39,452 and on Mar. 6, 1984 under accession number 39,626.

EXAMPLE 8

The procedure of Example 1 was repeated except that the IL-2 was recovered from *E. coli* K-12 strain that had been transformed with the plasmid pLW55 (deposited in the American Type Culture Collection on Nov. 18, 1983 under accession number 39,516). The amino acid sequence of this molecule is different from that of the native molecule in that it has an N-terminal methionine and the cysteine at position 125 has been changed to serine.

EXAMPLE 9

Des-Ala Ser$_{125}$ IL-2-producing *E. coli* were grown, the cells disrupted and the cellular debris recovered from the disruptate using the general procedures of Example 1. The cellular debris was suspended in 50 mM Tris, 1 mM EDTA pH 8.5 buffer at a ratio of about 1:4.5 (w/v). DTT was added to a final concentration of 25 mM. 8 M urea in the same buffer was slowly added with stirring to a final concentration of 4 M and then allowed to mix at room temperature for 30 min. After 30 min, the insoluble material remaining was centrifuged. The resulting paste was resuspended in 50 mM sodium phosphate buffer, 1 mM EDTA pH 7.0. The suspension was then solubilized by addition of solid SDS to a final concentration of 5% w/v.

The 5% SDS solution was diluted to 2% SDS with 0.1 M Na$_2$PO$_4$, pH 8.0. The protein concentration was determined, the pH was adjusted to 8.5, and DTT to 50 mM and EDTA to 2 mM were added. The mixture was heated to 40° C. under N$_2$ to reduce the IL-2. The mixture was then cooled and the pH was adjusted to 5.0.

Figure 3:
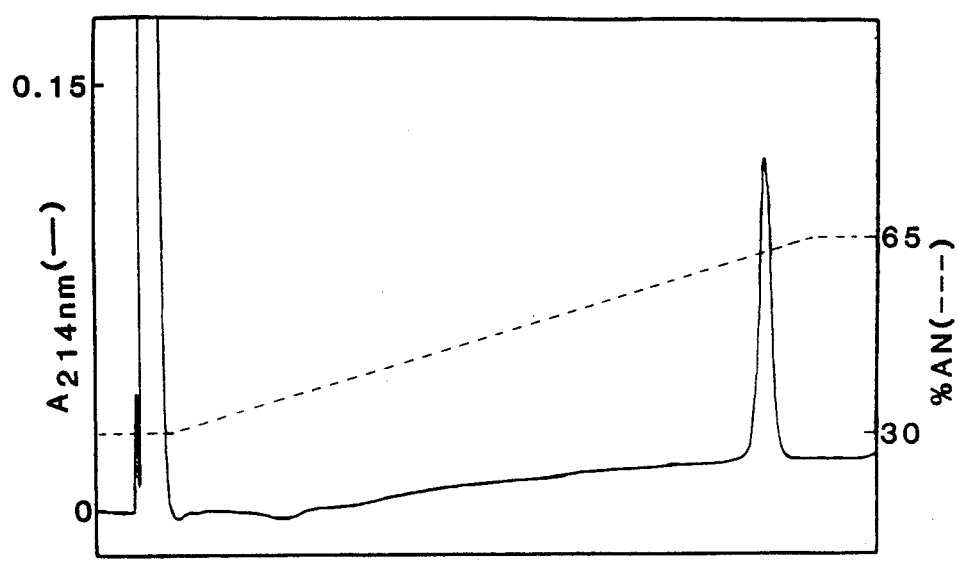
FIG. 3 is an HPLC chromatogram of the product of Example 9.

The solution was then extracted at a 1:1 ratio (v/v) with 2-butanol containing 1 mM DTT at room temperature. Residence time was 2–2.5 min. The extraction was carried out in a liquid-liquid phase separator using a flow rate of 200 ml/min. The organic extract was separated and its pH was adjusted to 8.0 with NaOH. The extract was then added slowly to 0.1% SDS in 10 mM Na$_2$PO$_4$, 2 mM DTT, pH 6 and stirred for 15–20 min. The resulting precipitate was separated and the resulting paste was resuspended in 5% SDS in PBS. The solution was clarified by centrifugation and reduced as above. Following reduction the solution was adjusted to pH 5.5 with acetic acid. The solution was purified by gel filtration using S-200 and G-25 columns. The resulting purified, reduced IL-2 was oxidized, and the oxidized product was purified by G-25 chromatography followed by RP-HPLC as in Example 3. The resulting purified recombinant IL-2 product has an IL-2 content greater than about 95% as determined by reducing SDS-PAGE analysis, an endotoxin content of less than about 0.1 nanograms/mg of IL-2, and it is substantially free of pyrogens as determined by the U.S.P. rabbit pyrogen test at a dosage of 3.3×10$^5$ U/kg. As previously indicated, the endotoxin content is less than about 5 nanograms, and preferably less than 0.01 nanograms endotoxin per 100,000 units IL-2 activity. Typically, the purified recombinant IL-2 products purified by the process of the invention have an IL-2 content greater than 98% as determined by reducing SDS-PAGE or RP-HPLC, as shown in FIG. 3 in addition to being substantially free of endotoxins and pyrogens as indicated above.

Figure 4:
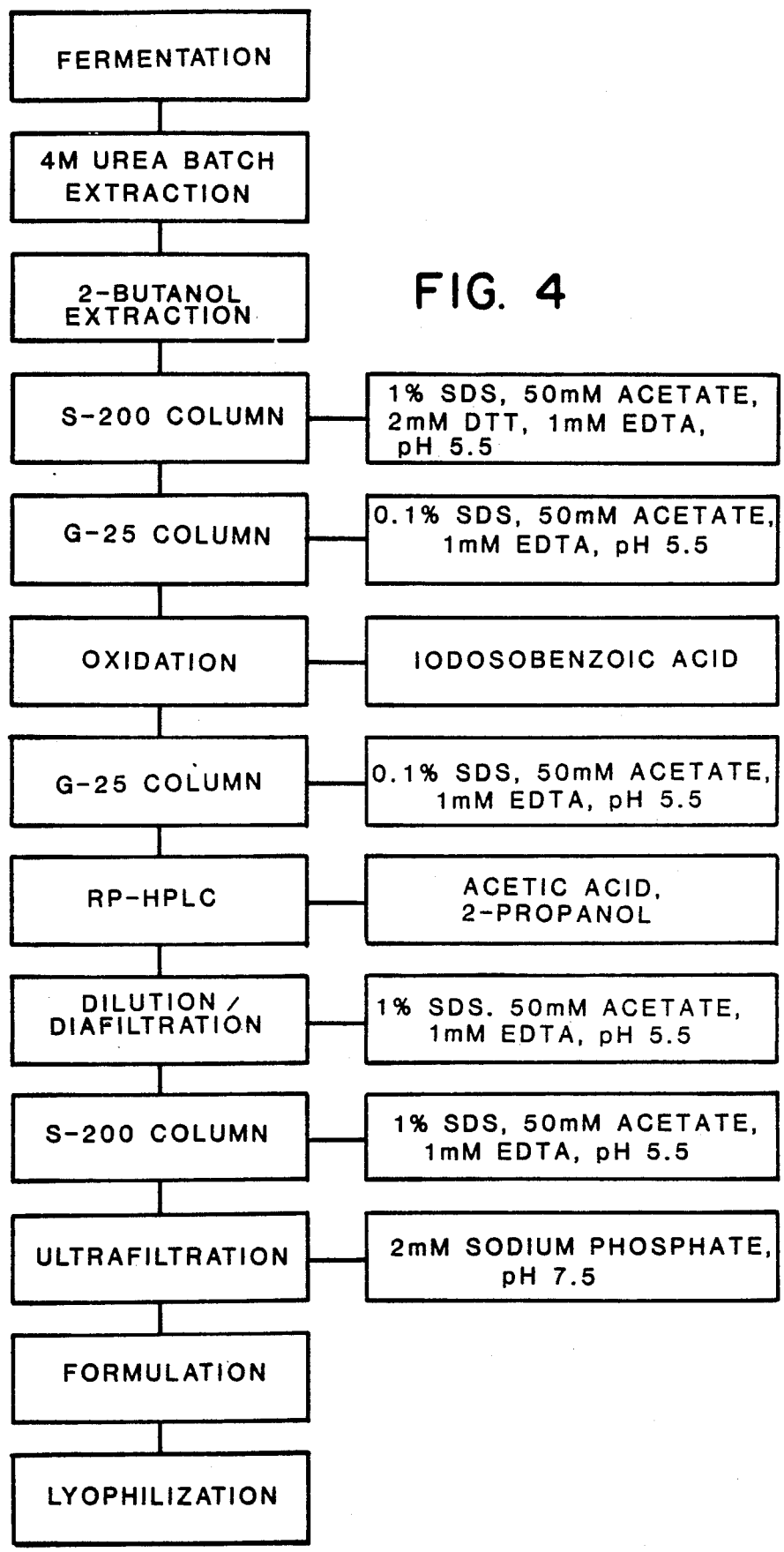
FIG. 4 is a flow diagram of a preferred procedure for processing microbially produced IL-2.

A variation of the process described in Example 9, such as might be used to produce IL-2 on a larger scale, is shown in FIG. 4. The process shown in FIG. 4 differs from that described in Example 9 as regards (1) minor changes in the buffers, (2) use of an acetic acid-propanol (Example 5) solvent system in the RP-HPLC, and (3) the inclusion of post-oxidation dilution/diafiltration S-200 gel filtration, and ultrafiltration steps. The process as shown in FIG. 4 may be modified with various refinements, for example, following the second S-200 column pass, in 1% SDS, the IL-2 solution is diluted 1:10 to give a 0.1% SDS concentration and then diafiltered against 10 mM phosphate buffer at a pH of 7.5 and 5 ppm SDS. The solution is then concentrated as required for appropriate use dosage.

Modifications of the above described modes for carrying out the invention that are obvious to those of skill in the fields of biochemistry, biochemical engineering, and related arts are intended to be within the scope of the following claims.

We claim:

1. A process for recovering purified, oxidized human IL-2 from a transformed microorganism containing the IL-2 comprising:
   (a) disrupting the cell membrane of the microorganism;
   (b) extracting the disruptate with an aqueous solution of a chaotropic agent that extracts non IL-2 proteins selectively from the cellular material and from the IL-2;
   (c) solubilizing the IL-2 in the solid phase of the extraction mixture with an aqueous solution of a solubilizing agent that forms a water soluble complex with the IL-2, said solution containing a reducing agent to thereby fully reduce the IL-2 in the complex;
(d) separating the reduced IL-2 from the resulting solution in the presence of the reducing agent;
(e) oxidizing the reduced IL-2;
(f) further purifying the resulting oxidized IL-2 product by gel filtration or reverse-phase high performance liquid chromatography as individual or combined steps; and
(g) recovering a purified oxidized recombinant human IL-2 composition having an IL-2 content of at least about 95% as determined by reducing SDS-PAGE analysis, an endotoxin content of less than about 0.1 nanograms/mg of IL-2 and substantially free of pyrogens as determined by the U.S.P. rabbit pyrogen test at a dosage of $3.3 \times 10^5$ U/kg.

2. The process of claim 1 wherein the chaotropic agent is urea.

3. The process of claim 2 wherein the concentration of urea in the extraction mixture is in the range of about 3.5 M to 4.5 M.

4. The process of claim 1 wherein step (b) is carried out at a basic pH.

5. The process of claim 4 wherein the pH is in the range of about 8.1 to about 8.5.

6. The process of claim 1 wherein the solubilizing agent is sodium dodecyl sulfate or sodium lauryl sarcosine.

7. The process of claim 1 wherein step (f) is carried out by reverse phase high performance liquid chromatography at a pH in the range of 2.1 to 2.3 using a bonded phase wide pore silica gel and a gradient solvent system comprising an organic acid and an organic solvent for eluting IL-2.

8. The process of claim 7 wherein the solvent system is acetic acid-propanol, trifluoroacetic acid-propanol, or trifluoroacetic acid-acetonitrile.

9. The process of claim 1 wherein step (f) is carried out by isolating an IL-2-containing fraction from the solution by gel filtration and purifying the resulting IL-2 from the fraction by reverse-phase high performance liquid chromatography.

10. The process of claim 9 wherein the reverse phase high performance liquid chromatography is carried out at a pH in the range of 2.1 to 2.3 using a bonded phase wide pore silica gel and a gradient solvent system comprising an organic acid and an organic solvent for IL-2.

11. The process of claim 10 wherein the solvent system is acetic acid-propanol, trifluoroacetic acid-propanol, or trifluoroacetic acid-acetonitrile.

12. The process of claim 1 including the following additional steps of:
(i) extracting the IL-2 from the aqueous solution of (c) with 2-butanol or 2-methyl-2-butanol;
(ii) acid precipitating the IL-2 from the extract; and
(iii) purifying the acid precipitated IL-2 by gel filtration.

13. The process of claim 12 wherein the chaotropic agent is urea, the concentration of urea in the extraction mixture is 3.5 M to 4.5 M, and the extraction of step (f) is carried out at a pH of 5 to 7.5.

14. The process of claim 12 including purifying the resulting oxidized gel filtered product by reverse-phase high performance liquid chromatography.

15. Purified recombinant human interleukin-2 (IL-2) composition wherein the IL-2 is unglycosylated and in oxidized form, having an IL-2 content of at least about 95% as determined by reducing SDS-PAGE analysis, an endotoxin content of less than about 0.1 nanogram/mg of IL-2 and substantially free of pyrogens as determined by the U.S.P. rabbit pyrogen test at a dosage of $3.3 \times 10^5$ U/kg.

16. The purified recombinant IL-2 composition of claim 15, wherein the IL-2 content is greater than about 98% as determined by reducing SDS-PAGE.

17. The purified recombination human IL-2 composition of claim 15, wherein the IL-2 content is greater than about 98% as determined by RP-HPLC.

18. The purified recombinant human IL-2 of claim 15, wherein the IL-2 is des-alanyl, serine$_{125}$IL-2.

19. The purified recombinant human IL-2 of claim 16, wherein the IL-2 is des-alanyl, serine$_{125}$IL-2.

20. The purified recombinant human IL-2 of claim 17 wherein the IL-2 is des-alanyl, serine$_{125}$IL-2.

21. The process of claim 7 wherein the solvent system is acetic acid-propanol.

* * * * *

UNITED STATES PATENT AND TRADEMARK OFFICE
CERTIFICATE OF CORRECTION

PATENT NO. : 4,569,790

DATED : February 11, 1986

INVENTOR(S) : Kirston Koths, James Thomson, Michael Kunitani, Kenneth Wilson, Wolf Hanisch It is certified that error appears in the above—identified patent and that said Letters Patent is hereby corrected as shown below:

On the first (title) page of the specification after the section titled "[73] Assignee: Cetus Corporation, Emeryville, California." insert the following section:

--[*] Notice: The portion of the term of this patent subsequent to July 23, 2002 has been disclaimed.--

On the first (title) page of the specification, in the section titled "Other Publications", line 6, change "Zaniguchi" to --Taniguchi--.

In column 12, claim 17, line 33, change "recombination" to --recombinant--.

Signed and Sealed this

Eleventh Day of November, 1986

Attest:

DONALD J. QUIGG

Attesting Officer     Commissioner of Patents and Trademarks